United States Patent [19]
Itoh

[11] Patent Number: 5,493,849
[45] Date of Patent: Feb. 27, 1996

[54] METHOD AND APPARATUS FOR CORKING UP SAMPLE-CONTAINED CONTAINERS

[76] Inventor: Teruaki Itoh, 5-25, Kokaihonmachi, Kumamoto-shi, Kumamoto-ken 860, Japan

[21] Appl. No.: 348,157

[22] Filed: Nov. 28, 1994

[30] Foreign Application Priority Data

Nov. 30, 1993 [JP] Japan .................................. 5-299487

[51] Int. Cl.$^6$ ............................... B65B 7/28; B67B 1/04
[52] U.S. Cl. ............... 53/489; 53/264; 53/307; 53/319; 53/367; 493/108; 493/308
[58] Field of Search ................... 53/489, 264, 319, 53/307, 367, 322, 324, 327, 328; 493/308, 102, 104, 108

[56] References Cited

U.S. PATENT DOCUMENTS 1,835,334  12/1931  Risser ..................................... 53/367
5,301,488   4/1994  Ruhl et al. .............................. 53/319

*Primary Examiner*—John Sipos
*Assistant Examiner*—John Paradiso
*Attorney, Agent, or Firm*—Nixon & Vanderhye

[57] ABSTRACT

A sample-contained container corking-up method of the present invention comprises a first step of holding each stopper supplied from a stopper supply means by a stopper holder and opposing an inserted portion of the stopper to the open top of the container which is supported at its corked-up position, a second step of pushing the inserted portion of the stopper, which has been opposed to the open top of the container by the first step, into it to a first predetermined position, while holding the stopper at a certain state by the stopper holder, a third step of releasing the stopper holder from the stopper and retreating the stopper holder to its waiting position after the stopper pushing operation conducted by the second step, and a fourth step of further pushing the inserted portion of the stopper into the container to a second predetermined position, deeper than the first one, while leaving the stopper holder retreated to the waiting position by the third step. A sample-contained container corking-up apparatus of the present invention comprises stopper supplying, positioning and pushing means and a control unit including first through third control means to automatically carry out the above-described method.

3 Claims, 3 Drawing Sheets

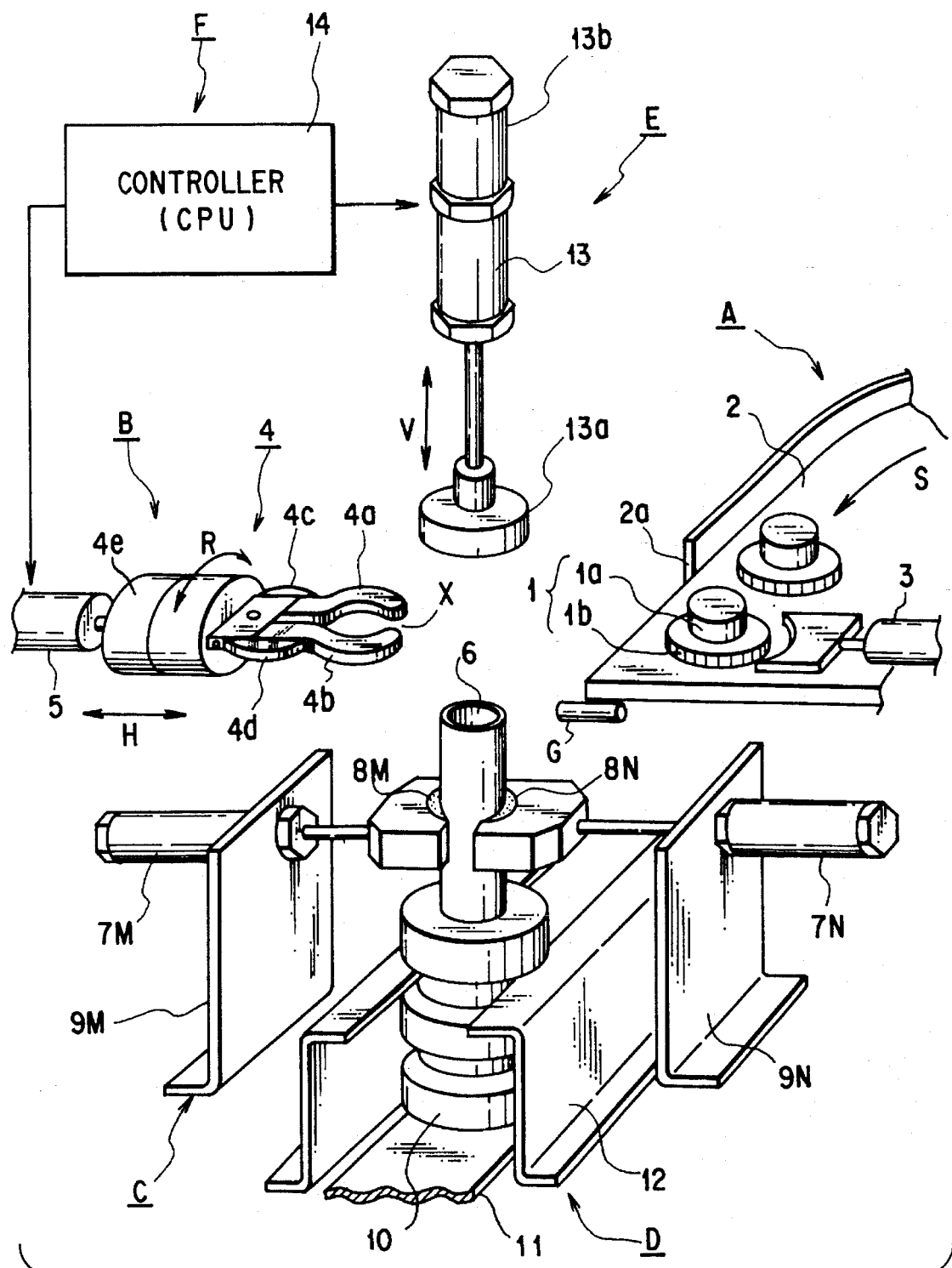
F I G. 1

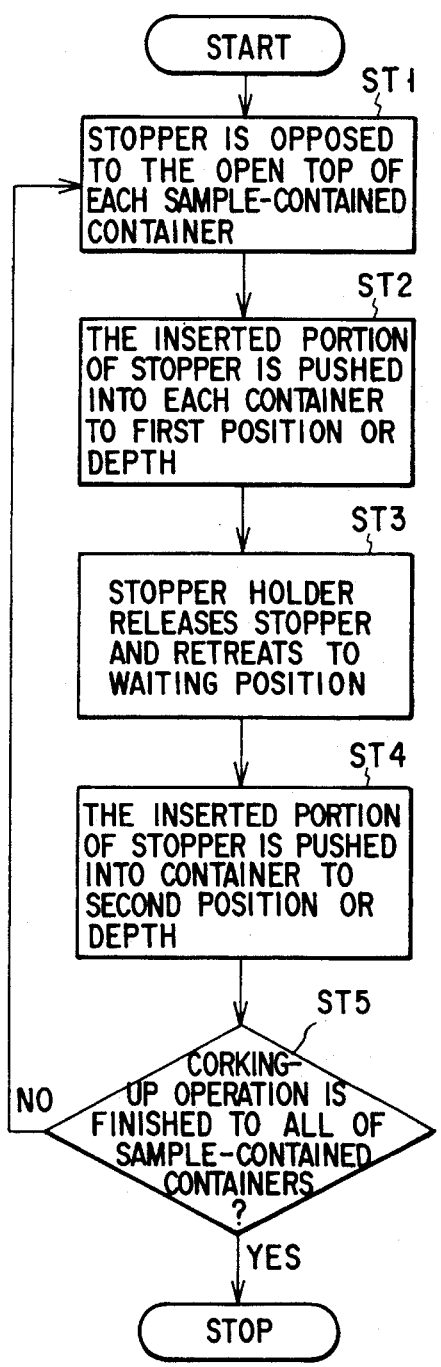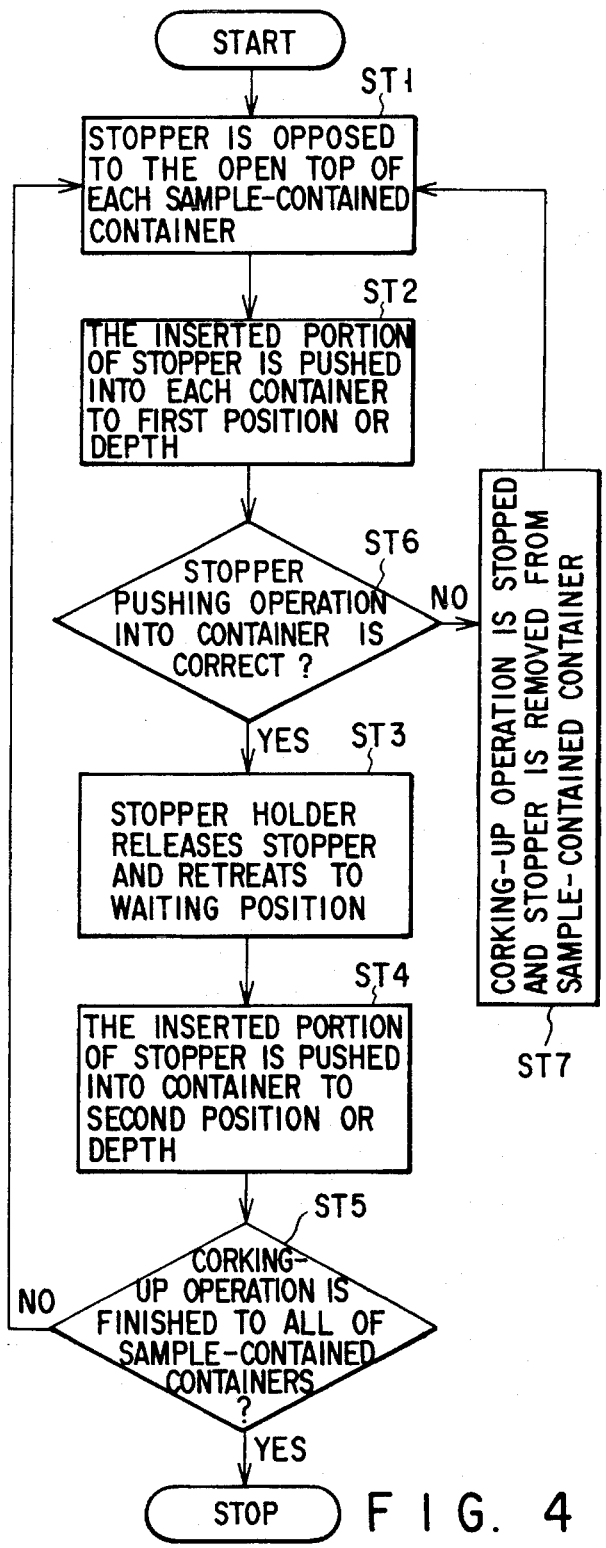
FIG. 3
FIG. 4

METHOD AND APPARATUS FOR CORKING UP SAMPLE-CONTAINED CONTAINERS

BACKGROUND OF THE INVENTION

1. Field of the Invention

The present invention relates to method and apparatus for automatically inserting a stopper or cork into the open end of each container such as the test tube in which sample like blood is contained to thereby cork up it.

2. Description of the Related Art

One of the conventional corking-up apparatuses of this kind is intended to mechanically push a stopper like a short round column, for example, into the open top of each sample-contained container.

In this conventional corking-up apparatus, however, no means is provided to hold the stopper correct at the corking-up time. In addition, the stopper is pushed into the open top of the container at a stroke. When the axial center of the stopper is not coincident with that of the sample-contained container or the stopper is not correct in size, therefore, it cannot enter into the open top of the container to thereby come out from it or it is forcedly and obliquely pushed into it to thereby make the corking-up incomplete.

In the case where samples such as blood are to be inspected in the inspection room, the inspection is often made about test tubes previously uncorked. After the inspection is finished, therefore, the test tubes must be corked to prevent samples from evaporating in them, particles from entering into them, and samples from spreading on the desk, for example, when they fall accidentally. A corking-up apparatus smaller in size, simpler in construction and capable of being more easily used in the inspection room, for example, is now asked accordingly.

SUMMARY OF THE INVENTION

The object of the present invention is therefore to provide a) a sample-contained container corking-up method capable of pushing the stopper into the open top of each sample-contained container to achieve a more quick and safer corking-up operation and b) a sample-contained container corking-up apparatus relatively smaller in size, simpler in construction and capable of automatically achieving its corking-up operation under a more sanitary and safer state and also more stably and reliably pushing the stopper into the open top of each sample-contained container.

This object can be achieved by sample-contained container corking-up method and apparatus as set below.

Sample-contained Container Corking-up Method

A sample-contained container corking-up method according to the present invention comprises a first step of holding each stopper supplied from a stopper supply means by a stopper holder and opposing an inserted portion of the stopper to the open top of the container which is supported at its corked-up position; a second step of pushing the inserted portion of the stopper, which has been opposed to the the open top of the container by the first step, into it to a first predetermined position, while holding the stopper at a certain state by the stopper holder; a third step of releasing the stopper holder from the stopper and retreating the stopper holder to its waiting position after the stopper pushing process by the second step; and a fourth step of further pushing the inserted portion of the stopper into it to a second predetermined position, deeper than the first one, while leaving the stopper holder retreated to the waiting position by the third step.

According to the sample-contained container corking-up method of the present invention having the above-described steps, the inserted portion of each stopper is pushed into the open top of each container while holding the stopper at a certain state by the stopper holder. Even when the direction of pushing force added to the stopper is a little shifted from the axial center line of the stopper, therefore, the stopper can be pushed into the open top of the container to the first predetermined position while being kept correct in posture, which will be hereinafter referred to as "a first state of the stopper inserted". Such shift of the stopper from the container in axial center line as causes stopper pushing error cannot be seen accordingly. This prevents the stopper from coming out from the open top of the container or from being obliquely and forcedly pushed into it to thereby make the corking-up operation incomplete.

While keeping the stopper under "the first state of the stopper inserted" under which the stopper holder releases the stopper and is retreated to its waiting position, the stopper is further pushed into the open top of the container to the second position, deeper than the first one, which will be hereinafter referred to as "a second state of the stopper inserted". The stopper holder is released and left remote from the stopper at this time. The stopper holder, therefore, cannot prevent the stopper from being pushed into the open top of the container fully to the second position.

Sample-contained Container Corking-up Apparatus

A sample-contained container corking-up apparatus according to the present invention comprises a means for supplying stoppers one by one each having a portion inserted into the open top of each container; a stopper positioning means for holding each of the stoppers successively supplied from the stopper supply means by a stopper holder and opposing the inserted portion of the stopper to the open top of the container, which is supported at its corked-up position, while holding the stopper at a certain state; a means for pushing the inserted portion of the stopper, which has been positioned by the stopper positioning means, into the open top of the container; and a control unit for controlling stopper pushing and positioning processes of both stopper pushing and positioning means. And the control unit also includes a first control means for causing the stopper pushing means to push the inserted portion of the stopper, which has been opposed to the open top of the container by the stopper positioning means, into the open top of the container to the first predetermined position, while holding the stopper at the certain state by the stopper holder, a second control means for releasing the stopper holder from the stopper and retreating the holder to its waiting position after control is conducted by the first control means, and a third control means for causing the stopper pushing means to push the inserted portion of the stopper into the open top of the container to the second position, deeper than the first one, after control is made by the second control means.

According to the sample-contained container corking-up apparatus of the present invention having the above-described arrangement, the corking-up operation conducted relative to each sample-contained container by the corking-up method can be made automatic, more stable and reliable.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 shows the apparatus for corking up each sample-contained container according to an embodiment of the present invention;

FIG. 3 is a flow chart showing how a first corking-up method according to the present invention is carried out; and FIG. 4 is a flow chart showing how a second corking-up method according to the present invention is carried out.

DETAILED DESCRIPTION OF THE PREFERRED EMBODIMENTS

Sample-contained Container Corking-up Apparatus

Figure 2:
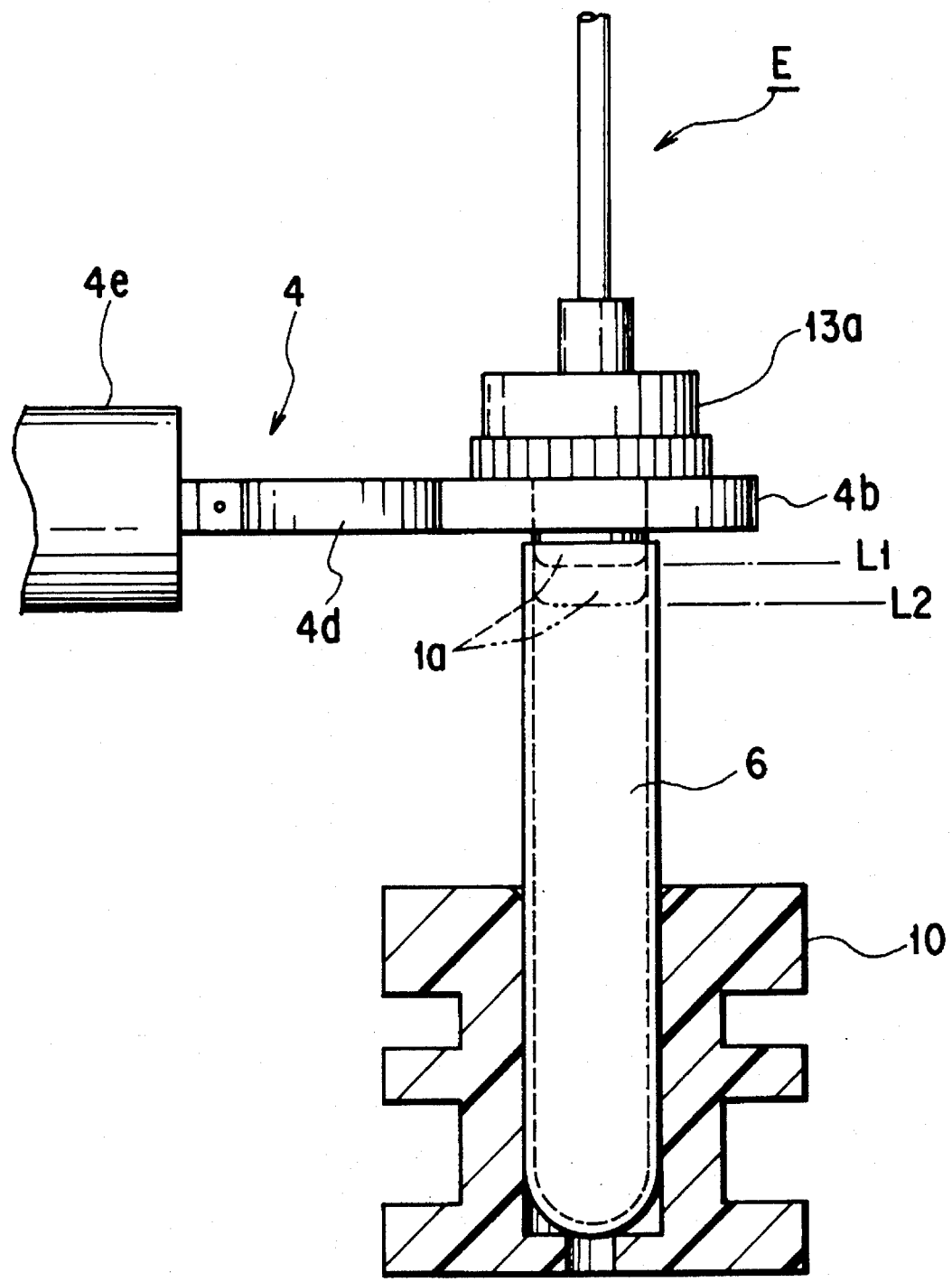
FIG. 2 is a side view showing a main portion of the apparatus partly sectioned.

FIG. 1 shows the container corking-up apparatus according to an embodiment of the present invention and FIG. 2 is a side view showing a main portion or cylindrical holder of the apparatus partly sectioned. Each section of the apparatus is automatically controlled by a control computer unit (not shown), for example.

In FIG. 1, A represents a stopper supply means, B a stopper positioning means, C a sample-contained container support means, D a carrier system, E a stopper pusher means, and F an operation control unit (controller).

The stopper supply means A supplies a plurality of stoppers 1 one by one to the terminal end of a parts feeder 2, as shown by an arrow S. Each stopper 1 is made by erosion-proof silicon rubber, normal rubber or other resilient materials and it comprises a cap 1b contacted with the open top of each sample-contained container 6 such as the test tube which will be described later, and an inserted portion 1a projected from one side of the cap 1b and inserted into the open top of each container 6. This stopper 1 which has been carried to the terminal end of the parts feeder 2, while keeping its portion 1a upside, is pushed at a certain timing from the terminal end of the parts feeder 2 through a feeder outlet 2a by a pusher unit 3 of the air piston/cylinder device type.

The stopper positioning means B comprises a stopper holder 4 and a unit 5 of the air piston/cylinder device type to horizontally reciprocate the stopper holder 4, as shown by arrows H. The stopper holder 4 has a pair of arms 4a and 4b freely opened and closed in a horizontal plane. A pair of springs 4c and 4d are attached to outer sides of the paired of arms 4a and 4b to usually urge them to be closed. When the inserted portion 1a of the stopper 1 is forced into a gap X between them, therefore, they are opened to hold the outer circumference of the inserted portion 1a between them. The paired arms 4a, 4b and springs 4c, 4d are attached to a front rotary section of a drive mechanism 4e such as the rotary solenoid. When the rotary drive mechanism 4e operates, therefore, the paired arms 4a and 4b can be turned by 180 degrees, as shown by arrows R.

The sample-contained container support means C has a pair of chucks 7M and 7N of the air piston/cylinder device type, between which the sample-contained container 6 is held and sandwiched. 8M, 8N denote resilient pads and 9M, 9N support plates. The container 6 is carried to its corking-up position by the carrier system D, which comprises a belt conveyor 11 and guide rails 12, while being held by a cylindrical holder 10. It is stopped at the corking-up position by a stopping means (not shown) and held there between the chucks 7M and 7N.

The stopper pusher means E is a pusher 13 of the air piston/cylinder device type, which has a cylinder 13b and a piston 13a movable up and down, as shown by arrows V, relative to the cylinder 13b. When the pusher 13 moves down, therefore, the cap 1b of the stopper 1 which has been positioned by the stopper positioning means B is pushed down to force its inserted portion 1a into the open top of the sample-contained container 6.

The operation control means F includes a controller 14, which is a central processing unit (CPU), to control operations of both stopper positioning and pushing means B and E.

The operation control means F causes the stopper pusher means E to push the inserted portion of the stopper 1, which has been positioned relative to the open top of the container 6 by the stopper holder 4, into the container 6 to a first position L1, as shown in FIG. 2. This is a first control done by the operation control means or unit F. It then causes the stopper holder 4 to be released from the stopper 1 and the stopper holder 4 to be retreated to the waiting position. This is a second control. It further causes the stopper pusher means E to push the inserted portion of the stopper 1 into the container to a second position L2, deeper than the position L1, as shown in FIG. 2. This is a third control.

According to the sample-contained container corking-up apparatus having the above-described arrangement, its corking-up operation will be attained as follows.

The stopper 1 which has been carried, while keeping its inserted portion up, to the terminal end of the parts feeder 2 is pushed outside through the outlet 2a by the pusher system 3. At the same time, the stopper holder 4 which is opposed to the pusher system 3 is driven forward by the drive system 5. The inserted portion 1a of the stopper 1 is thus pushed into the gap X between the paired arms 4a and 4b, which are opened to receive the inserted portion 1a of the stopper 1 between them. The stopper 1 thus held between them is turned upside down by 180 degrees by the rotary drive 4e. The inserted portion 1a of the stopper 1 is therefore opposed to the open top of the sample-contained container 6 which has been supported stable at its corked-up position by the chucks 7M and 7N. The stopper pusher 13 is then moved down to push the inserted portion 1a of the stopper 1 into the open top of the container 6 to the first position L1. When this is finished, the stopper holder 4 releases the stopper 1 and it is retreated to its waiting position. The stopper pusher 13 is further moved down to push the inserted portion 1a of the stopper 1 into the open top of the container 6 to the second position L2.

Sample-contained Container Corking-up Method

FIG. 3 is a flow chart showing a first corking-up method according to the present invention. As shown in FIG. 3, it includes first through fifth steps ST1–ST5.

At the step ST1, the stopper 1 supplied by the stopper supply means A is held by the stopper holder 4 and its inserted portion 1a is opposed to the open top of the sample-contained container 6. At the step ST2, the inserted portion 1a is pushed into the open top of the container 6 to the first position L1 by the stopper pusher 13, while being held by the stopper holder 4. At the third step ST3, the stopper holder 4 releases the stopper 1 and it is retreated to its waiting position. At the fourth step ST4, the inserted portion 1a of the stopper 1 is further pushed into the open top of the container 6 to the second position L2. At the fifth step ST5, it is checked whether or not the corking-up operation relative to the container 6 is finished. When not finished, it is returned to the first step ST1 and again repeated from the step ST1 to the fifth step ST5. Each container can be thus automatically corked up.

FIG. 4 is a flow chart showing a second corking-up method according to the present invention. It further includes sixth and seventh steps ST6 and ST7 in addition to those of the first corking-up method. At the sixth step ST6, it is checked whether or not the stopper 1 is correctly inserted into the container 6, while seeing the stopper pushing process at the second step ST2. When correctly inserted, the process advances to the third step ST3 but when not correctly inserted, the corking-up operation is stopped and it is again repeated from the first step ST1 after the stopper 1 is removed from the sample-contained container 6.

Merits of the Embodiments

1) The first corking-up method according to the present invention comprises the first step ST1 of holding the stopper 1, which is supplied by the stopper supply means A, by the stopper holder 4 and opposing its inserted portion 1a to the open top of the sample-contained container 6 which is at its corked-up position, the second step ST2 of pushing the inserted portion 1a into the open top of the container 6 to the first position L1, while holding the stopper 1 by the stopper holder 4, the third step ST3 of releasing the stopper holder 4 from the stopper 1 and retreating the holder 4 to its waiting position, and the fourth step ST4 of further pushing the inserted portion 1a into the open top of the container 6 to the second position L2.

According to the first corking-up method of the present invention, therefore, the inserted portion 1a of the stopper 1 is pushed into the open top of the sample-contained container 6 while holding the stopper 1 correct by the stopper holder 4. Even when the direction of pushing force added to the stopper 1 is a little shifted from the axial center line of the stopper 1, therefore, the stopper 1 can be pushed into the container 6 to the first position L1, while being held correct in posture. This is "the first state of the stopper inserted". No insertion or push error of the stopper 1 can be thus caused by the shift of stopper's axial center line from that of the container 6. Further, the stopper 1 cannot come out from the open top of the container 6 and it cannot be obliquely forced into the container to incompletely cork up it.

While keeping the stopper 1 under "the first state of the stopper inserted" under which the stopper holder 4 released from the stopper 1 and the holder 4 is retreated to the waiting position, it is further pushed into the open top of the container 6 to the second position L2, deeper than the first one L1. This is "the second or final state of the stopper inserted". Under this state, it is released from the stopper 1 and the holder 4 is kept remote from the stopper 1. Therefore, its insertion or push operation cannot be disturbed by the stopper holder 4 and it can be thus pushed into the container fully to the second position L2.

2) In addition to those steps which are mentioned in the above item 1), the second corking-up method according to the present invention further includes the sixth step ST6 of checking whether or not the stopper 1 is correctly pushed into the open top of the container 6, while seeing the stopper pushing process conducted by the second step ST2, and advancing the corking-up operation to the third step ST3 when the stopper is correctly pushed, and the seventh step ST7 of stopping the operation and returning it to the first step ST1 after the stopper 1 is removed from the container 6, when not correctly pushed.

According to the second corking-up method, therefore, it is checked at all times whether or not the stopper 1 is correctly pushed into the open top of the container 6 to the first position L1 and the corking-up operation advances to the next step when correctly pushed, but when not correctly pushed, it is returned to the first step after the stopper 1 and the container are returned to their original positions. Even when the stopper 1 is not correct in size or it is forced obliquely into the container 6, therefore, it can be stopped from being pushed into the container 6 to the second or final position L2. This also prevents the sample-contained container 6 from being broken by its forced insertion.

3) The sample-contained container corking-up apparatus according to the present invention comprises the means A for supplying stoppers 1 one by one, each having the portion 1a pushed into the open top of each container 6, the stopper positioning means B for opposing the inserted portion 1a of the stopper 1 to the open top of the container 6 which is supported at its corked-up position, while holding the stopper 1 supplied from the stopper supply means A by the stopper holder 4, the means E for pushing the inserted portion 1a of the stopper 1, which has been positioned by the stopper positioning means B, into the open top of the container 6, and the control unit F for controlling stopper pushing and positioning processes of both means B and E. The control unit F includes the first control means for causing the means E to push the inserted portion 1a of the stopper 1, which has been opposed to the open top of the container 6 by the stopper positioning means B, into the container 6 to the first predetermined position L1, while holding the stopper 1 by the stopper holder 4, the second control means for causing the stopper holder 4 to release the stopper 1 and also be retreated to its waiting position after the control operation of the first control means, and the third control means for causing the means E to push the inserted portion 1a into the container 6 to the second position L2, deeper than the first one L1, after the control operation of the second control means.

According to the sample-contained container corking-up apparatus having the above-described arrangement, therefore, the corking-up operation conducted relative to each sample-contained container 6 by the above-described corking-up method can be made automatic and more stable and reliable.

4) The corking-up apparatus according to the above item 3) further includes means G for checking whether or not the stopper 1 is correctly pushed into the container to the first position L1 and causing the corking-up operation to be again repeated from the first step ST1, using another stopper, when not correctly pushed.

According to the corking-up apparatus, therefore, the corking-up operation is again started from the first step ST1 when the stopper 1 is not correctly pushed into the container 6 to the first position L1. This can leave each container safer and it is quite preferable from practical viewpoint.

5) The corking-up apparatus according to the above item 3) includes the stopper supply means A for successively carrying and supplying stoppers 1, each having the cap 1b contacted with the open top of each container 6 and the portion 1a projected from one side of the cap 1b and inserted into the open top of the container, while keeping the portion-projected side of the cap 1b upward, and the stopper positioning means B for holding each stopper 1 by the stopper holder 4 in such a way that the inserted portion 1a of the stopper 1 supplied from the stopper supply means A is sandwiched and held between the arms 4a and 4b of the stopper holder 4, and turning it upside down by 180 degrees to direct its inserted portion 1a downward and oppose it to the open top of each container 6 which is erected at its corked-up position.

According to the corking-up apparatus, therefore, stopper 1 can be more stably carried because their caps 1b which have a large area are seated on the carrier means. In addition, stopper 1 holding can be made more stable and reliable because the inserted portion 1a projected from each cap 1b and having a relatively small diameter is held by the stopper holder 4. Further, each stopper 1 is turned upside down by 180 degrees while being held by the stopper holder 4. The axial center line of the inserted portion 1a of the stopper 1 cannot be therefore shifted from that of the container 6. This also enables the inserted portion 1a to be opposed more correctly to the open top of the container 6.

6) The corking-up apparatus includes those variation which are a stopper of the round or square column type and drive sources of the hydraulic type for the pusher system 3 and others.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method of corking up each of sample-contained containers comprising:

a first step of holding each stopper supplied from a stopper supply means by a stopper holder and opposing an inserted portion of the stopper to the open top of the container which is supported at its corked-up position;

a second step of pushing the inserted portion of the stopper, which has been opposed to the open top of the container by the first step, into it to a first predetermined position, while holding the stopper at a certain state by the stopper holder;

a third step of releasing the stopper holder from the stopper and retreating the stopper holder to its waiting position after the stopper pushing operation conducted by the second step; and a fourth step of further pushing the inserted portion of the stopper into the container to a second predetermined position, deeper than the first one, while leaving the stopper holder retreated to the waiting position by the third step.

2. The sample-contained container corking-up method according to claim 1, further including a fifth step of checking whether or not the stopper is correctly pushed into the open top of the container, while viewing the stopper pushing process conducted by the second step, and advancing the corking-up operation to the third step when the stopper is correctly pushed into the container, and a sixth step of stopping the corking-up operation by a stopping means and commanding the operation to be repeated from the first step, when it is checked by the fifth step that the stopper is not correctly pushed into the container, after the stopper is removed from the container.

3. An apparatus for corking up each of sample-contained containers comprising:

a means for supplying stoppers one by one each having a portion inserted into the open top of each container;

a stopper positioning means for holding each of the stoppers successively supplied from the stopper supply means by a stopper holder and opposing the inserted portion of the stopper to the open top of the container, which is supported at its corked-up position, while holding the stopper at a certain state;

a means for pushing the inserted portion of the stopper, which has been positioned by the stopper positioning means, into the open top of the container; and a control unit for controlling stopper pushing and positioning processes of both stopper pushing and positioning means, said control unit including a first control means for causing the stopper pushing means to push the inserted portion of the stopper, which has been opposed to the open top of the container by the stopper positioning means, into the open top of the container to a first predetermined position, while holding the stopper at a certain state by the stopper holder, a second control means for releasing the stopper holder from the stopper and retreating the holder to its waiting position after control is conducted by the first control means, and a third control means for causing the stopper pushing means to push the inserted portion of the stopper into the open top of the container to a second predetermined position, deeper than the first one, after control is made by the second control means.

* * * * *